(12) United States Patent
Bansal

(10) Patent No.: US 9,816,999 B2
(45) Date of Patent: *Nov. 14, 2017

(54) NEO ANTIBODIES FOR DIAGNOSTIC IMAGING OF TISSUE INJURY

(71) Applicant: NOVELMED THERAPEUTICS, INC., Cleveland, OH (US)

(72) Inventor: Rekha Bansal, Cleveland, OH (US)

(73) Assignee: Novelmed Therapeutics, Inc., Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 14/605,694

(22) Filed: Jan. 26, 2015

(65) Prior Publication Data

US 2015/0139899 A1  May 21, 2015

Related U.S. Application Data

(63) Continuation of application No. 13/990,313, filed as application No. PCT/US2011/062418 on Nov. 29, 2011, now Pat. No. 8,940,490.

(60) Provisional application No. 61/417,682, filed on Nov. 29, 2010.

(51) Int. Cl.
| | |
|---|---|
| G01N 33/53 | (2006.01) |
| G01N 33/68 | (2006.01) |
| G01N 33/74 | (2006.01) |
| A61K 49/00 | (2006.01) |
| A61K 51/10 | (2006.01) |
| C07K 16/18 | (2006.01) |

(52) U.S. Cl.
CPC ......... *G01N 33/6896* (2013.01); *A61K 49/00* (2013.01); *A61K 51/1018* (2013.01); *C07K 16/18* (2013.01); *G01N 33/6878* (2013.01); *G01N 33/74* (2013.01); *C07K 2317/33* (2013.01); *C07K 2317/92* (2013.01); *G01N 2333/4716* (2013.01); *G01N 2800/16* (2013.01)

(58) Field of Classification Search
None
See application file for complete search history.

(56) References Cited

U.S. PATENT DOCUMENTS

| | | | |
|---|---|---|---|
| 5,707,810 | A | 1/1998 | Smart et al. |
| 7,341,839 | B2 | 3/2008 | Hollyfield et al. |
| 7,351,524 | B2 | 4/2008 | Hageman et al. |
| 2006/0067935 | A1 | 3/2006 | Ambati |
| 2006/0135423 | A1 | 6/2006 | Ambati |
| 2009/0081211 | A1 | 3/2009 | Capmagne |
| 2009/0175875 | A1 | 7/2009 | Etemad-Gilbertson et al. |
| 2010/0291106 | A1* | 11/2010 | Etemad-Gilbertson ... C07K 16/18 424/172.1 |
| 2011/0182908 | A1 | 7/2011 | Hageman |
| 2012/0135430 | A1 | 5/2012 | Zhang |
| 2013/0029912 | A1* | 1/2013 | Holers .............. C07K 14/47 514/13.5 |

FOREIGN PATENT DOCUMENTS

| | | |
|---|---|---|
| CN | 101355956 A | 1/2009 |
| CN | 101848937 A | 9/2010 |
| WO | 95/17673 A1 | 6/1995 |
| WO | 9517673 A1 | 6/1995 |
| WO | 2004112572 A2 | 12/2004 |
| WO | 2005108988 A2 | 11/2005 |
| WO | 2009102488 A2 | 8/2009 |
| WO | 2010029162 A1 | 3/2010 |
| WO | 2010135717 A2 | 11/2010 |

OTHER PUBLICATIONS

Tamerius et al. (J. Immunology 1985 vol. 135, p. 2015-2019).*
Rostagno et al. J. Biol. Chem. 2002 vol. 277 p. 49782-49790.*
Takematsu et al. (Dermatology 1992 vol. 185, p. 246-250).*
Hendrik, P.N. Scholl, et al., "Systematic Complement Activation in Age-Related Macular Degeneration", PLOS one, vol. 3(7), e2593, Jul. 2, 2008.
Sobha Sivaprasad, et al., "Estimation of Systematic Complement C3 Activation in Age-Related Macular Degeneration" Arch Ophthalmol., vol. 125, pp. 515-519, Apr. 30, 2007.
Bora, Nalini S., "The Role of Complement in Ocular Pathology", Semin Immunopathol (2008) 30:85-95.
Johnson, Lincoln V., "Complement Activation and Inflammatory Processes in Drusen Formation and Age Related Macular Degeneration", Exp. Eye Res. (2001) 73, 887-896.
Katschke, Kenneth J., et al., "Structural Functional Analysis of a C3b-Specific Antibody that Selectively Inhibits the Alternative Pathway of Complement", The Journal of Biochemical Chemistry, 2009, pp. 1-15.
Opperman, Martin, et al., "Quantitation of Components of the Alternative pathway of complement (APC) by Enzyme-Linked Immunosorbent Assays", Journal of Immunological Methods, 133 (1990) 181-190.
Shamonki, Jaime M., et al., "Excessive Complement Activation is Associated with Placental Injury in Patients with Antiphospholipid Antibodies" American Journal of Obstetrics & Gynecology, Feb. 2007.
Nozaki, Miho, et al., "Drusen Complement Components C3a and C5a Promote Choroidal neovascularization", PNAS, Feb. 14, 2006, vol. 103, No. 7.
3rd Chinese Office Action dated Jun. 18, 2015.
Scholl, et al. "Systemic Complement Activation in Age-Related Macular Degeneration", PLoS ONE, Jul. 2008, vol. 3, issue 7, e2593.
Supplementary European Search Report dated Apr. 17, 2015.
Johnson, et al. "Complement Activation and Inflammatory Processes in Drusen Formation and Age Related Macular Degeneration", Exp. Eye Res. (2001) 73, 887-896.

(Continued)

*Primary Examiner* — Jacob Cheu
(74) *Attorney, Agent, or Firm* — Tarolli, Sundheim, Covell & Tummino LLP

(57) ABSTRACT

A method for diagnosing the development of a tissue injury in a subject comprising administering a sample of neoantibodies to the subject's tissue for the purpose of detecting the presence of neoepitopes bearing complement proteins.

18 Claims, 14 Drawing Sheets

(56) References Cited

OTHER PUBLICATIONS

Bora, et al. "The role of complement in ocular pathology", Semin Immunopathol (2008) 30:85-95.
Dako, "Monoclonal Mouse Anti-Human C5b-9, Clone aE11, Code No. 0777", M0777/RUO/HEW/10-06-04, pp. 1-2, 2004.
Falk, Ronald J., et al., Neoantigen of the Polymerized Ninth Component of Complement—The American Society for Clinical Investigation, Inc., vol. 72, Aug. 1993, 560-573.
Johnson, Lincoln V., et al., "A Potential Role for Immune Complex Pathogenesis in Drusen Formation", Exp. Eye Res. (2000) 70, 441-449.
European Office Action dated Jul. 25, 2016.
E.T. Molenarr, et al., "Complement Activation in Patients With Rheumatoid Arthritis Mediated in Part by C-Reactive Protein" vol. 44, No. 5, May 2001, pp. 997-1002.
Office action for European Patent Application No. 11 844 421.5-1404, dated May 31, 2017.
Canadian Office Action dated Jun. 23, 2017.

* cited by examiner

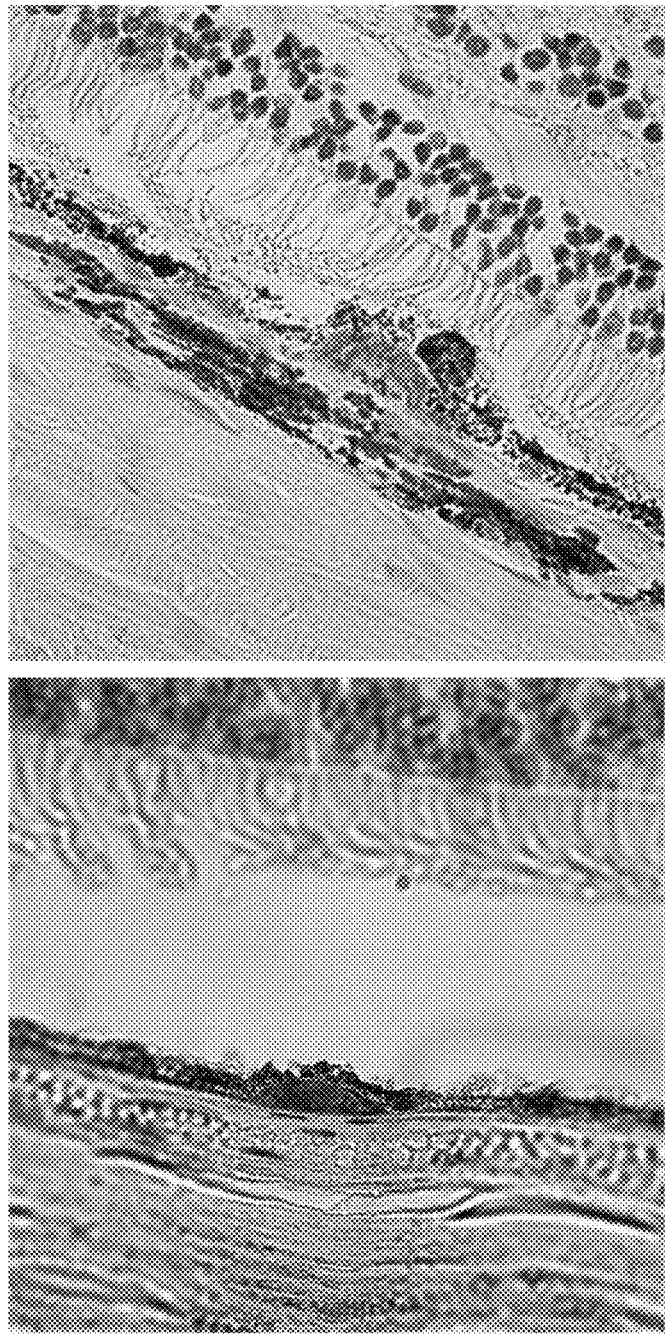
Fig. 14 Neo Anti Polymeric C9, Detects Pathological Drusen

NEO ANTIBODIES FOR DIAGNOSTIC IMAGING OF TISSUE INJURY

RELATED APPLICATION

This application claims priority from U.S. Provisional Application No. 61/417,682, filed Nov. 29, 2010, the subject matter of which is incorporated herein by reference in its entirety.

TECHNICAL FIELD

This application relates to compositions and methods for diagnosing or identifying tissue injury in a subject, and, more particularly, to compositions and methods of diagnosing or identifying complement-mediated tissue injury in a subject.

BACKGROUND

Complement-mediated tissue injury occurs when complement activation completes the terminal pathway to generate a membrane attack complex (MAC, C5b-9). These complexes are known to cause tissue injury. Complement plays an important pathological role in several disease indications including macular degeneration, rheumatoid arthritis, myocardial infarction, and organ reperfusion injury. It is difficult to determine the site, intensity, and extent of tissue damage using non-invasive techniques. In human subjects, generally it is difficult to use other non-invasive techniques to determine internal tissue injury, including injuries to the eye. However, diagnostic procedure such as those presented in this application can be applied to reveal such information.

SUMMARY

This application relates to neoantibodies or fragments thereof and to the use of neoantibodies or fragments thereof for the diagnosis or identification of tissue injury in a subject in a non-invasive or minimally invasive manner. In some embodiments, the neoantibodies or fragments thereof can be used to identify and/or diagnose diseases, such as macular degeneration, an eye disease commonly found in the elderly. The site of complement-mediated pathology is expected to be clearly identified by the neoantibodies or fragments thereof. The site of pathology can be determined by the presence of deposited C5b-9 and other neoepitopes on proteins formed as a result of complement activation.

In some examples, the disease can be age-related macular degeneration (AMD) and drusen can be a site of pathology in the ocular tissue. Drusen is a yellow or white extracellular deposit located in the macular region between the RPE and the Bruch's membrane, around either the optic disc or the periphery. There are two categories of drusen; those that are pathological and others that are no pathological. Neoantibodies or fragments thereof described herein can detect the presence of pathological drusen by detecting complement protein activation products associated with pathological drusen.

Neoantibodies or fragments thereof in accordance with the application can target unique epitopes called "neoepitopes" that are formed upon complement activation and that are not present on complement proteins prior to complement activation. Neoepitopes can include unique epitopes that are formed on complement fragments as the result of cleavage of complement proteins and which are not present on the parent complement protein as well as unique epitopes that are formed in complement activation products as the result of aggregation or complexing of complement proteins or fragments upon complement activation and that are not present on complement proteins prior to complement activation.

For example, during complement activation, C3 is converted into C3a and C3b. Both C3a and C3b can be detected by anti-C3 antibodies that detect epitopes common to both C3a and C3b. C3a and C3b also include neoepitopes that appear as a result of C3 cleavage and are not present in the parent C3 molecule. The detection of neoepitopes of complement activation products can be used in the detection of complement-mediated tissue injury in a subject. Similarly, C5a and C5b contain neoepitopes that are formed as a result of C5 cleavage. Neoantibodies or fragments thereof targeted against C5a and C5b do not cross react with the C5 protein even though both are derived from C5. Factor B is cleaved into Ba and Bb by factor D. Neoantibodies or fragments thereof to Ba and Bb can be used in the detection of complement mediated tissue injury. Although antibodies that bind Ba and Bb will also bind with factor B, neo anti-Ba and neo anti-Bb will not bind factor B.

The same is true for neoantibodies or fragments thereof specific for C5b-9, also known as the MAC complex. The MAC consists of proteins C5, C6, C7, C8, and C9. Antibodies to C6, C7, and C8 will detect the presence of C5b-9. Such antibodies will not distinguish between their respective free proteins found in the blood or MAC complex. Neoantibodies or fragments thereof that can specifically detect MAC complex C5b-9 can include anti-polymeric C9 or anti-C5b-9. Non-neoantibodies will also recognize and detect these proteins. However, only neo anti-polymeric C9 and neo anti-C5b-9 can distinguish between MAC complex C5b-9 and its constituent complement proteins in the subject. These neoantibodies or fragments thereof will not recognize the soluble forms of constituent proteins that make up the MAC.

Blood samples taken from a patient can be analyzed for the presence of complement proteins using various anti-complement antibodies. However, soluble complement proteins are constitutively present in blood, regardless of tissue damage. Antibodies not specific to a neoepitope formed upon complement activation will detect the soluble form of these proteins and will not be reliable for detection of pathology. Neoantibodies or fragments thereof described herein can be used to obtain a specific profile of complement-mediated tissue damage.

In some embodiments, neoantibodies or fragments thereof described herein can be used to detect the presence of pathological drusen in tissue by administering an appropriate amount of the neoantibodies or fragments thereof. Complement proteins including MAC (C5b-9) are found to be associated with drusen, the Bruch's membrane, the basal surface of the RPE, and the sub-RPE in ocular tissue. Factors C3, C5, C9, and the C5b-9 terminal complex have been found associated with drusen. Other complement-related molecules CR1, CR2, clustrin, and vitronectin have been found associated with drusen. Additional complement pathway-associated molecules localized in Bruch's membrane and/or drusen include C3d, C6, C7, C8, C9, factor D, factor H, factor L, factor B, clusterin, and mannose binding protein. Further, some complement pathway-associated molecules such as CD21, CD35, CD55/decay accelerating factor, and CD59/protectin are present in the basal surface of the RPE.

Neoantibodies or fragments thereof for detecting drusen can include anti-neo polymeric C9 antibodies which only recognizes a neoepitope formed by polymeric C9 in the C5b-9 complex. In complement-mediated pathology, tissue damage would occur as a result of C5b-9 deposition on the tissue. This deposition, and therefore the extent of tissue damage, could be visualized using anti-polymeric C9. These antibodies can be tagged with an agent to increase the sensitivity of the detection.

Ocular related disorders that can be diagnosed with imaging methods described herein include age-related macular degeneration (AMD), North Carolina macular dystrophy, Sorsby's fundus dystrophy, Chemical Stargardt's disease, pattern dystrophy, Best disease, dominant drusen, malattia leventinese, retinal detachment, chorioretinal degenerations, retinal degenerations, photoreceptor degenerations, RPE degenerations, Mucopolysaccharidoses, rod-cone dystrophies, cone-rod dystrophies, and cone degenerations.

Aberrant activation of the alternative complement pathway has been implicated in several pathological situations that are both acute and chronic in nature. Elevated levels of alternative pathway activation byproducts have been found in several injury indications such as extracorporeal circulation injuries, cardiovascular diseases, transplantation rejections, eye diseases, hemolytic diseases, respiratory diseases, neurological diseases, trauma-induced injuries, systemic inflammation & bone related disorders, renal diseases, reperfusion injuries of organs, reproduction and urogenital diseases, dermatologic diseases, gastrointestinal diseases, endocrine diseases, or other diseases indications indicated below. Neobodies or fragments thereof described herein can be used in the detection of these complement activation by products associated with these injuries.

Examples of extracorporeal circulation injuries include: Post-cardiopulmonary bypass inflammation, post-operative pulmonary dysfunction, cardiopulmonary bypass, hemodialysis, leukopheresis, plasmapheresis, plateletpheresis, heparin-induced extracorporeal LDL precipitation (HELP), postperfusion syndrome, extracorporeal membrane oxygenation (ECMO), systemic inflammatory response, and multiple organ failure.

Examples of cardiovascular diseases include: Kawasaki disease, Henoch-Schonlein purpura nephritis, vascular leakage syndrome, percutaneous coronary intervention (PCI), ischemia-reperfusion following acute myocardial infarction, myocardial infarction, atherosclerosis, vasculitis, immune complex vasculitis, sepsis, arteritis, aneurysm, cardiomyopathy, Takayasu's arteritis, dilated cardiomyopathy, venous gas embolus (VGE), Wegener's granulomatosis, and Behcet's syndrome.

Examples of transplantation injuries include: transplant rejection, graft versus host disease, xenotransplantation of organs or grafts, allotransplantation of organs or grafts, and hyperacute rejection.

Examples of eye diseases include: Age-related macular degeneration (wet and dry), choroidal neurovascularization (CNV), corneal neovascularization, retinal neovascularization, retinal damage, diabetic retinopathy, diabetic retinal microangiopathy, diabetic macular edema, histoplasmosis of the eye, uveitis, pathological myopia, central retinal vein occlusion (CRVO), retinal pigment epithelium (RPE), and Purtscher's retinpathyretinopathy.

Examples of hemolytic diseases include: catastrophic anti-phospholipid syndrome (CAPS), cold agglutinin disease (CAD), autoimmune thrombotic thrombocytopenic purpura (TTP), endotoxemia, atypical hemolytic uremic syndrome (aHUS), paroxysmal nocturnal hemoglobinuria (PNH), sepsis, septic shock, sickle cell anemia, hemolytic anemia, hypereosinophilic syndrome, anti-phospholipid syndrome (APLS).

Examples of respiratory diseases: Asthma, eosinophilic pneumonia, hypersensitivity pneumonia, allergic bronchitis bronchiecstasis, reactive airway disease syndrome, respiratory syncytial virus (RSV) infection, parainfluenza virus infection, rhinovirus infection, adenovirus infection, allergic bronchopulmonary aspergillosis (ABPA), tuberculosis, parasitic lung disease, adult respiratory distress syndrome, chronic obstructive pulmonary disease (COPD), emphysema, bronchitis, cystic fibrosis, interstitial lung disease, acute respiratory distress syndrome (ARDS), transfusion-related acute lung injury, acute lung injury, byssinosis, and asbestos-induced inflammation.

Examples of neurological diseases include: myasthenia gravis, multiple sclerosis, Guillain-Barre syndrome, stroke, Alzheimer's disease, multifocal motor neuropathy (MMN), Huntington's disease, amyotrophic lateral sclerosis (ALS), Parkinson's disease, degenerative disc disease (DDD), cranial nerve damage from meningitis, variant Creutzfeldt-Jakob Disease (vCJD), idiopathic polyneuropathy, and neuropathic pain.

Examples of trauma-induced injuries include: hemorrhagic shock, hypovolemic shock, spinal cord injury, neuronal injury, cerebral trauma, cerebral ischemia reperfusion, crush injury, wound healing, severe burns, and frostbite.

Examples of systemic inflammation & bone Inflammation & Bone related disorders include: systemic lupus erythematosus (SLE), rheumatoid arthritis, systemic juvenile rheumatoid arthritis, osteoarthritis, osteoporosis, sarcoid.

Examples of renal diseases include: renal reperfusion injury, post-streptococcal glomerulonephritis (PSGN), Goodpasture's disease, membranous nephritis, Berger's Disease/IgA nephropathy, mesangioproliferative glomerulonephritis, membranous glomerulonephritis, membranoproliferative glomerulonephritis, and renal cortical necrosis (RCN).

Examples of reperfusion injuries of organs can include, but not limited to, heart, brain, kidney, and liver.

Examples of reproduction and urogenital diseases include: spontaneous abortion, fetomaternal tolerance, preeclampsia, sensory bladder disorders, and interstitial cystitis.

Examples of dermatologic diseases include: pemphigoid, epidermolysis bullosa acquisita, autoimmune bullous dermatoses, bullous pemphigoid, scleroderma, angioedema, hereditary angioneurotic edema (HAE), erythema multiforme, herpes gestationis, Sjogren's syndrome, psoriasis, dermatomyositis, eosinophilic spongiosis, atopic dermatitis, and dermatitis herpetiformis.

Examples of gastrointestinal diseases include: Crohn's disease, Celiac Disease/gluten-sensitive enteropathy, Whipple's disease, intestinal ischemia, inflammatory bowel disease, and ulcerative colitis.

Examples of endocrine diseases include: Hashimoto's thyroiditis, juvenile lymphocytic thyroiditis, type I diabetes mellitus, stress anxiety, diseases affecting prolactin, growth factor, and adrenocorticotropin release, pancreatitis, Addison's disease, and insulin resistance.

Examples of other diseases can include: Goodpasture's disease, Parkinson's disease, burn injury, Alzheimer's disease, urticaria, Huntington's disease, Berger's disease, cardiac Surgery, hypovolemic shock, Crohn's disease, hyperacute rejection in organ transplantation, thermal injury, severe asthma, bowel inflammation, percutaneous coronary intervention, heparin-induced extracorporeal membrane oxygenation, and anaphylactic shock.

Other embodiments of the application relate to neoantibodies or fragments thereof that are conjugated to labeling agents injected into the blood stream to be able to detect the pathological tissue of interest. In some embodiments, neoantibodies can include full IgG or fragments thereof. Neoantibodies or fragments thereof can be conjugated to labeling, imaging, or contrast agents, such as indocyanin green, 99 mTc, immunoPET, and detected by imaging methods specific for such labeling, imaging, or contrast agent.

Still other embodiments of the application relate to methods for the diagnosis of macular degeneration-related disorders in a subject by detecting fragments of complement activation in a tissue. The presence of drusen of any size is detectable with neoantibodies or fragments thereof. Such antibodies should not cross react with free parent proteins from which the neoepitope is derived. In some embodiments, the neoantibody specifically binds to complement pathway-associated molecules within the ocular tissue. In other embodiments, abnormal levels of neoepitope only are detected.

Another embodiment of the application relates to methods for diagnosis, or identifying a predisposition to the development of a macular degeneration-related disorder in a subject. These methods detect the presence of a neoepitope containing complement protein and/or fragments in ocular tissue. The ocular tissue can be from a patient with macular degeneration. The macular degeneration-associated neoantigen containing molecule would be selected from the group consisting of C3b, iC3b, C3dg, C3c, C5b, C5b-9, C3a, and C5a. In some embodiments, tissue samples from a subject suffering from disease can be used for diagnostic purposes. The tissue samples may include body fluids and fluids of the eye.

In another embodiment, the detection step entails using labeled neoantibodies or fragments thereof for detecting neoepitopes in the eye tissue of patients with an eye disease of the macula. In this method, the labeled neoantibody fragment binds a macular degeneration-associated molecule (or a neoantigen-) flowing detection using an imaging system. Some methods comprise detecting at least one macular degeneration-associated neoepitopes in the subject. Some methods further include examining the subject with an ophthalmologic imaging procedure.

Still other embodiments of the application relate to kits for diagnosing or identification of a predisposition for the development of a macular degeneration-related disorder in a subject. The labeled antibody will include at least one macular degeneration-associated neoantigen, a neoantibody that is labeled with an imaging agent, and a media sample, which establishes the binding of the neoantibody with the neoantigen.

DESCRIPTION OF THE DRAWINGS

FIG. 14 shows the binding characteristics of Neo Anti-Polymeric C9, wherein Neo Anti-Polymeric C9 detects pathological Drusen.

DETAILED DESCRIPTION

Figure 1:
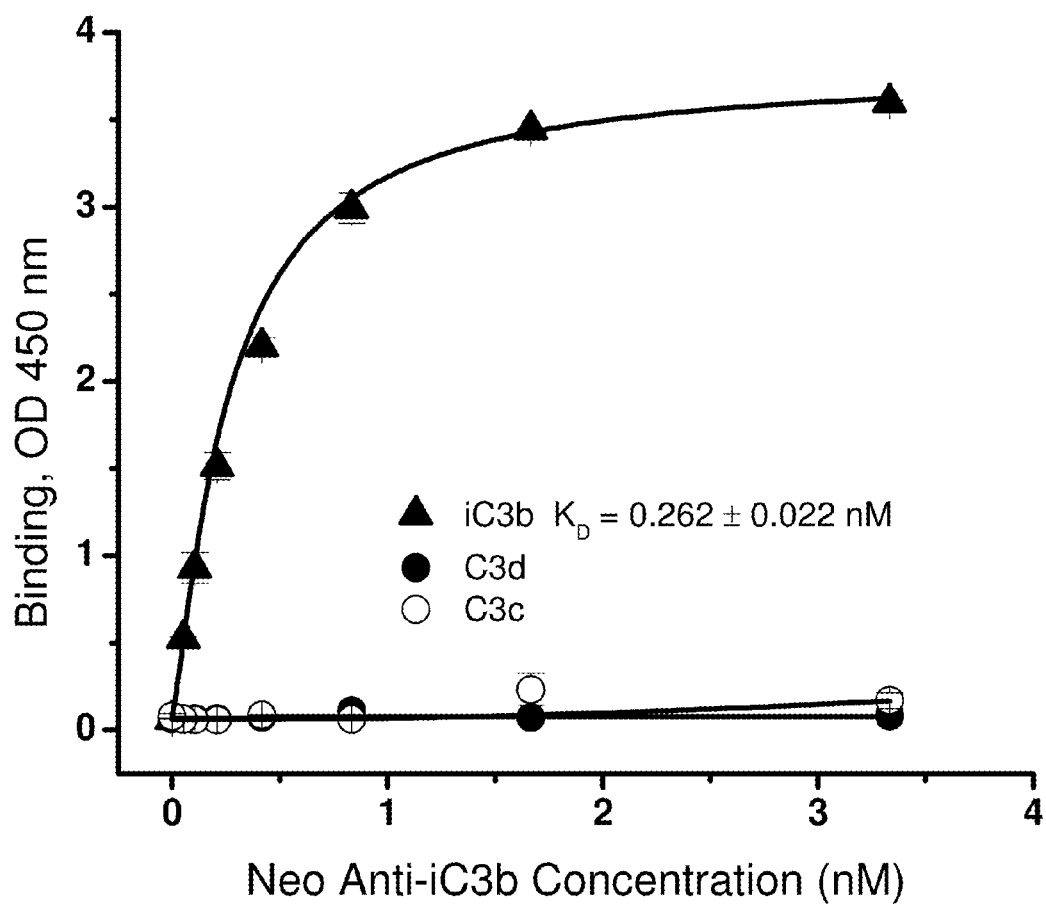
FIG. 1 shows the binding characteristics of Neo Anti-iC3b, wherein Neo Anti-iC3b detects substrate-bound iC3b but not C3c and C3d.

As used herein, the term "antibody" includes full length monoclonal antibodies, polyclonal antibodies, nanobodies and multi-specific antibodies. Biological antibodies are usually hetero-tetrameric glycoproteins of about 150,000 Daltons, composed of two identical light (L) chains and two identical heavy (H) chains. The two heavy chains are linked together by disulfide bonds, and each heavy chain is linked to a light chain by a disulfide bond. Each full-length IgG molecule contains at least two binding sites for a specific target or antigen. Light chains are either kappa or the lambda. Both light chains contain a domain of variable amino acid sequences, called the variable region (variously referred to as a "$V_L$," "$V_{kappa}$", or "$V_{lambda}$-region") and a domain of relatively conserved amino acid sequences, called the constant region ("CL-region"). Similarly, each heavy chain contains a variable region ("$V_H$-region") and three constant domains ("$C_{H1}$-," "$C_{H2}$-," and "$C_{H3}$-regions") and a hinge region.

As used herein, the term "antibody fragment", "antigent-binding fragment", or "fragment thereof" of an antibody refers to a segment of a full-length antibody, generally called as the target binding or variable region. Examples include Fab, Fab', F(ab')$_2$ and Fv fragments. An "Fv" fragment is the minimum antibody fragment which contains a complete target recognition and binding site. Fab, Fab', and F(ab')$_2$ lack the F$_c$ regions. Fragments can be prepared from full-length antibody by protease digestion. Fragments may be produced using standard recombinant DNA methodology by those skilled in the art.

As used herein, the term "epitope" refers to a site on a protein, polypeptide, complement factor, complement fragment to which antibody and fragments thereof bind and perform the functional activity. The term epitope is the same as "antigenic site", and "antibody binding site".

As used herein, "Fab fragment" refers to the constant domain of the light chain and the first constant domain of the heavy chain. Fab' fragments differ from Fab fragments by the few extra residues at the carboxyl terminus of the heavy chain CH1 domain including one or more cysteines from the antibody hinge region. F(ab') fragments are produced by cleavage of the disulfide bond at the hinge cysteines of the F(ab')$_2$ pepsin digestion product.

As used herein, the term "functional fragment" of an antibody refers to an antibody fragment having qualitative biological activity in common with a full-length antibody.

As used herein, the term "human consensus framework" refers to a framework which represents the most commonly occurring amino acid residue in a selection of human immunoglobulin VL or VH framework sequences. Generally, the selection of human immunoglobulin VL or VH sequences is from a subgroup of variable domain sequences.

As used herein, a "humanized antibody" refers to an antibody consisting of mostly human sequences, except for CDR1, CDR2, and CDR3. All framework regions are also humanized. A chimeric antibody comprises murine CDRs, murine framework regions, and human constant regions. Collectively, chimeric antibodies contain murine both variable regions and human constant regions.

As used herein, the term "identical" or "substantially identical" with respect to an antibody chain polypeptide sequence may be construed as an antibody chain exhibiting at least 65%, 70%, 80%, 90% or 95% sequence identity to the reference polypeptide sequence present in the variable region of the antigen binding fragment. The term with respect to a nucleic acid sequence may be construed as a sequence of nucleotides exhibiting at least about 65%, 75%, 85%, 90%, 95% or 97% sequence identity to the reference nucleic acid sequence.

As used herein, the term "individual" or "subject" refers to a vertebrate, preferably a mammal and more preferably a human. Individuals amenable to treatment include those who are presently asymptomatic, but who are at risk of developing a symptomatic disorder in which the alternative complement pathway plays a role, or in which activation of the alternative complement pathway plays a role.

As used herein, the term "mammal" refers to any animal classified as a mammal includes humans, higher primates, domestic and farm animals, horses, pigs, cattle, dogs, cats and ferrets, etc. In one embodiment of the invention, the mammal is a human.

As used herein, "monoclonal antibody" refers to a homogeneous population of antibodies. Such antibodies are highly specific and are directed against a single target antigen. These monoclonal antibodies are homogeneously produced by the hybridoma culture, uncontaminated by other immunoglobulins. Monoclonal antibodies can also be produced by other procedures such as phase display by well known methods.

Embodiments described herein include compositions and methods that comprise neoantibodies or fragments thereof, which bind novel (neo) epitopes on protein molecules. Neoantibodies or fragments thereof that bind to complement activation products include those antibodies that bind novel epitopes within a complement activation product that are not present in the parent complement protein or molecule. For example, neoantibodies or fragments thereof described herein can bind C3b but not C3, C3a but not C3, C3d but not C3, C3c but not C3, iC3b but not C3, C5b but not C5, C5a but not C5, and C5b-9 but not C5, C6, C7, C8, C9.

To detect ongoing complement activation within the eye, highly target specific monoclonal antibodies are needed that can specifically identify an activated, deposited proteins without binding to free proteins. Such new and specific site-driven monoclonal antibodies are one of the targets of the antibodies described herein. These antibodies are also known as neoantibodies. These monoclonal antibodies bind novel epitopes on the proteins formed after activation has occurred. Monoclonal antibodies that do not recognize C3 but recognize a neoantigen can be selected from the group consisting of anti-C3b, anti-iC3b, anti-C3c, and anti-C3d, and monoclonal antibodies that do not recognize C5, C6, C7, C8, and C9 but do recognize "polymeric C9" or other neoepitopes of the C5b-9 complex.

Neoantibodies or fragments thereof described herein can detect the presence of neoantigens in eye tissue with the use of imaging systems. A neoantibody tagged with an imaging agent can be injected or administered to the eye or be administered via any administration route. The neoantibody can then bind a neoantigen epitope on complement proteins formed within tissue where complement is activated. In the ocular tissue, the activated complement proteins (neoantigens) are indicative of pathology. Thus identification of neoepitopes in a tissue can translate to identification of pathological site. Ocular tissue can be examined for neoantibody binding (e.g., RPE, choroid) using sophisticated imaging techniques.

It is possible to distinguish between neoantigens formed as a result of classical (CP) versus alternative (AP) complement pathway activation. If the classical complement pathway is activated then neoantigens formed specific to CP activation can be identified. If the alternative pathway is activated then neoantigens specific to AP activation can be identified.

Many different antibodies can be generated to target a large protein. Neoantibodies or fragments thereof are selected by neoepitope-based screening. For example, anti-C3b, anti-iC3b, anti-C3c, and anti-C3d should only recognize and detect neoepitopes and not the parent molecule C3. Both monoclonal and polyclonal antibodies can be can be used in neoepitope-based screening. Neoantigens contain novel epitopes that a) are absent in parent molecules and b) are only present in the newly formed daughter molecule. Examples of neoantigens include C3b, iC3b, C3c, C3dg. Although these molecules are derived from the C3 molecule they carry a novel epitope that is specific to the individual protein fragment.

Neoantibodies or fragments thereof against various macular degeneration-associated neoantigens, such as (a) C3a, C3b, iC3b, C3c, C3dg; (b) Ba, Bb; (c) C5b, C5a; (d) C5b-9; and (e) C4b can be distinguished from their parent molecule. These molecules can be detected by respective neoantibodies or fragments thereof specific to each of the molecules mentioned above. Neoanntibodies described herein will not detect C3, factor B, C5, C6, C7, C8, and C9.

For example, C3a, C3b, iC3b, C3c, and C3dg are split products of C3. Therefore anti-C3 monoclonal and polyclonal antibodies may cross-react with C3a, C3b, iC3b, C3c, and C3dg. Neoantibodies or fragments thereof described do not cross-react with C3 and only bind C3a, C3b, iC3b, C3c, and C3dg, respectively. Formation of C3 fragments exposes a novel motif within the fragment called a neoepitope. Such epitopes can only be detected by neoantibodies.

In C5b-9, the complex consists of a split product of C5 and proteins such as C6, C7, C8, and multiple monomers of C9. Thus, anti-C6, C7, and C8 will detect the C5b-9 complex. These antibodies can also detect free proteins and therefore would not be able to distinguish the presence of free proteins from those that are part of the C5b-9 complex. Neoantibodies or fragments thereof described herein only include the neoantibodies or fragments thereof that recognize novel epitope within the complex, i.e., anti-C5b, anti-polymeric C9, and anti-C5b-9.

Anti-C5b antibodies can recognize both free C5 and C5b. Neoantibodies or fragments thereof described herein can recognize C5b but not C5. Anti-polymeric C9 can recognize the C5b-9 and not free C9. Anti-C5b-9 can recognize MAC and not individual constituent proteins.

Some embodiments of the application include methods for diagnosing, or determining a predisposition to development of a macular degeneration-related disorder by detecting the presence of complement neoantigens. The indications that can be diagnosed with these methods include: age-related macular degeneration (AMD), North Carolina macular dystrophy, Sorsby's fundus dystrophy, Stargardt's disease, pattern dystrophy, Best disease, dominant drusen, and Malattia Leventinese. Other ocular pathologies that can be diagnosed with these methods include: retinal detachment, chorio-retinal degenerations, retinal degenerations, photoreceptor degenerations, RPE degenerations, mucopolysaccharidoses, rod-cone dystrophies, cone-rod dystrophies, and cone degenerations.

The methods described herein can be used for large scale screening of a population for the presence of macular degeneration-related disorders. The methods can also be used for monitoring a response to treatment for subjects who have been diagnosed and are undergoing therapy. The methods of detecting the presence of neoantigens targeted against several macular degeneration-associated molecules can be performed in combination, with methods for the detection of other phenotypic or genotypic markers correlated with macular degeneration-related disorders or drusen-associated diseases.

In other embodiments, neoantibodies or fragments thereof described herein can be labeled with a label, contrast, or imaging agent. The use of chemical entities to label proteins is well known. These labeled neoantiboides can be used in in vitro, ex vivo, and in vivo assays. Using similar chemistry, chemical entities can be conjugated site-specifically to IgG, Fab, F(ab')2, Fab', and single chain neoantibodies. The use of Fab' to produce bio-conjugates is known. Such bio-conjugates can be used to detect the presence of neantibody targets within the tissue and or body fluids. These bio-conjugates can be administered to the human body and visualized via imaging methods. Neoantibodies or fragments thereof can also be conjugated to chemical entities. Chemical entities include radioisotopes or imaging fluorophores which can be detected using a variety of imaging procedures.

In some examples, the label can include technetium-99m. Technetium-99m is generally available as sodium pertechnetate. The pertechnetate can be contacted with a reducing agent, such as stannous chloride. This reduces the technetium to a +3, +4 or +5 oxidation state in the presence of the protein, chelating agent or like substance which is to be radiolabeled. The technetium can be maintained in this reduced state in order to maintain the chemical bond between the technetium molecule and the neoantibody being radiolabeled. The technetium can be firmly bound to the neoantibody such that the reduced technetium is not transferred to other molecules or other proteins present in the assay, patient's blood or other media in which the radiolabeled substance will be utilized. Several different methods have been described to radiolabel monoclonal antibodies with technetium-99m.

In some embodiments, detection of complement-mediated pathology using neoantibodies or fragments thereof can provide an accurate depiction of the site and degree of disease progression in both dry and wet AMD. Neoantibodies or fragments thereof described herein can also be used to measure the degree of progression or regression of disease in a treated individual. Neoantibodies or fragments thereof described herein can also detect the onset and progression of AMD. Neoantibodies or fragments thereof can be used in a formulation appropriate for the eye.

By way of example, fundoscopic imaging can distinguish between rapid versus slow progression of the disease in an individual. Specifically, sites of pathologic injury and atrophic patches of injury can be easily identified. A clarifying example would be the scenario of an elderly woman with choroidal neovascularization (CNV) in one eye and soft drusen in the other eye. The diagnostic method described herein can distinguish the relative degree of disease progression between the CNV eye and the drusen eye based on the levels of neoantibody deposition. By comparing the relative levels of the neoantibody via imaging, a clinician can determine if the eye containing only drusen will progress to CNV. The methods described herein can reveal information indicating disease progression and the potential for transition of pathological drusen deposits into CNV.

Rupture of the Bruch's membrane is a key pathological marker for determining the conversion from dry, non-exudative AMD into wet, exudative AMD. Rupture of the Bruch's membrane is associated with clinical findings of fluid or hemorrhagic exudates in the retina and choroid. The methods described herein can therefore identify a site on Bruch's membrane rupture through the detection of membrane areas that show high levels of neoantibody deposition. The information from imaging studies that use neoantibodies or fragments thereof can give insight whether clinical intervention—surgical or pharmacologic is required.

EXAMPLES

Example 1: Binding of Neo Anti-iC3b Antibody to iC3b but not to C3c and C3d

Neo anti-iC3b antibody binds to the neoepitope on antigen iC3b. This antibody did not bind to C3c or C3d. The C3 molecule upon activation converts into C3b and C3a. C3b is inactivated by factor I to generate iC3b. Neo anti-iC3b recognized a neoepitope on the iC3b molecule. This neoantibody did not bind C3c suggesting that the alpha and beta chains of the C3b molecule do not possess the neoepitope. The absence of cross-reactivity of neo anti-iC3b to C3c and C3d suggests that the antibody recognizing epitope is lost when the C3c and C3d are produced. Neo anti-iC3b is expected to exhibit similar binding behavior on tissues in vivo.

Polystyrene microtiter plates were coated with human factors iC3b, C3d, and C3c (Complement Technology, Tyler, Tex.) each at (0.5 µg/50 µl/well) in PBS overnight at 4° C. After aspirating the protein solutions, wells were blocked with PBS containing 1.0% bovine serum albumin (BSA, Sigma-Aldrich, St. Louis, Mo.) for 1 hour at room temperature. Wells without protein coating similarly blocked and served as background controls. Aliquots of neo anti-iC3b (Quidel Corporation, San Diego, Calif.) at varying concentrations in blocking solution were added to the wells. Following a 1 hour incubation at room temperature, the wells were washed with PBS.

Protein-bound neo anti-iC3b was detected by the addition of peroxidase conjugated goat anti-mouse antibody at 1:2000 dilution. Following a 1 hour incubation at room temperature, the plate was washed and 100 µl of 3,3',5,5'-tetramethyl benzidine (TMB) substrate (Kirkegaard & Perry Laboratories, Gaithersburg, Md.) was added. After incubation for 30 minutes at room temperature, the TMB reaction was quenched by the addition of 100 μl of 1 M phosphoric acid, and the plate was read at 450 nm on a microplate reader (SPECTRAMAX 250, Molecular Devices, Sunnyvale, Calif.). The estimated Kd of neo anti-iC3b binding to various substrate-bound proteins was based on the concentration of neo anti-iC3b at 50% maximal binding (Microcal Origin, Northampton, Mass.).

Neo anti-iC3b bound iC3b with an affinity of 262 pM but did not bind C3d and C3c, therefore neo anti-iC3b is highly specific. The apparent binding constant from these data, defined as the concentration of neo anti-iC3b needed to reach half-maximal binding, is approximately 200-300 pM. The data is shown in FIG. 1.

Example 2: Binding of Neo Anti-C3d Antibody to C3d but not C3c

Neo anti-C3d antibody did not bind the C3c molecule which contains the alpha and beta chains of the C3b molecule. Upon cleavage of C3b, C3c and C3d are formed. The C3d molecule is released from the C3b molecule to produce C3c. Neo anti-C3d specifically binds the C3d molecule and does not bind C3c.

Polystyrene microtiter plates were coated with human C3d and C3c (Complement Technology) each at (0.5 μg/50 μl/well) in PBS overnight at 4° C. After aspirating the protein solutions, wells were blocked with PBS containing 1.0% BSA (Sigma-Aldrich) for 1 hour at room temperature. Wells without protein coating were similarly blocked and served as background controls. Aliquots of neo anti-C3d (Quidel Corporation) at varying concentrations in blocking solution were added to the wells. Following a 1 hour incubation at room temperature, the wells were washed with PBS.

Protein-bound neo anti-C3d was detected by the addition of peroxidase-conjugated goat anti-mouse antibody at 1:2000 dilution. Following a 1 hour incubation at room temperature, the plate was rinsed and 100 μl of TMB substrate (Kirkegaard & Perry Laboratories) was added. After incubation for 30 minutes at 25° C., the TMB reaction was quenched by the addition of 100 μl of 1 M phosphoric acid, and the plate was read at 450 nm on a microplate reader (SPECTRAMAX 250, Molecular Devices). The estimated Kd of neo anti-C3d binding to various substrate-bound proteins was based on the concentration of neo anti-C3d at 50% maximal binding (Microcal Origin).

Figure 2:
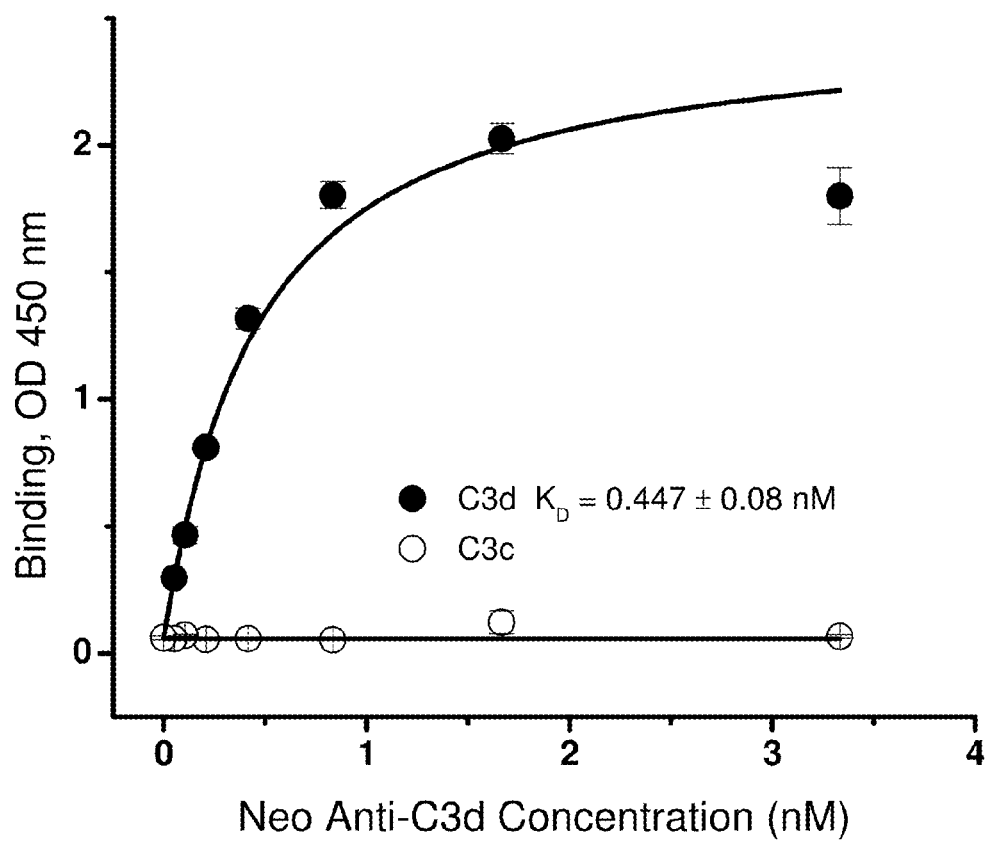
FIG. 2 shows the binding characteristics of Neo Anti-C3d, wherein in Neo Anti-C3d binds with C3d but not C3c.

Neo anti-C3d bonded to C3d with an affinity of 447 pM but did not bind C3c therefore neo anti-C3d is highly specific. The apparent binding constant from these data, defined as the concentration of neo anti-C3d needed to reach half-maximal binding, is approximately 350-550 pM. The data is shown in FIG. 2.

Example 3: Anti-Bb and Neo Anti-Bb have Differential Binding to Factor B

Neo anti-Bb antibody does not bind Factor B, however non-neo anti-Bb does bind factor B. Bb is an alternative pathway-specific protein and can be detected with the neo anti-Bb antibody.

Polystyrene microtiter plates were coated with human B at (0.5 μg/50 μl/well) (Complement Technology) in PBS overnight at 4° C. After aspirating the protein solutions, wells were blocked with PBS containing 1.0% BSA (Sigma-Aldrich) for 1 hour at room temperature. Wells without protein coating were similarly blocked and served as background controls. Aliquots of neo and non-neo anti-Bb (Quidel Corporation) at varying concentrations in blocking solution were added to factor B coated wells. Following a 1 hour incubation at room temperature, the wells were washed with PBS.

Factor B bound neo/non-neo anti-Bb was detected by the addition of peroxidase conjugated goat anti-mouse antibody at 1:2000 dilution. Following a 1 hour incubation at room temperature, the plate was washed and 100 μl of TMB substrate (Kirkegaard & Perry Laboratories) was added. After incubation for 30 minutes at room temperature, the TMB reaction was quenched by the addition of 100 μl of 1 M phosphoric acid, and the plate was read at 450 nm on a microplate reader (SPECTRAMAX 250, Molecular Devices).

Figure 3:
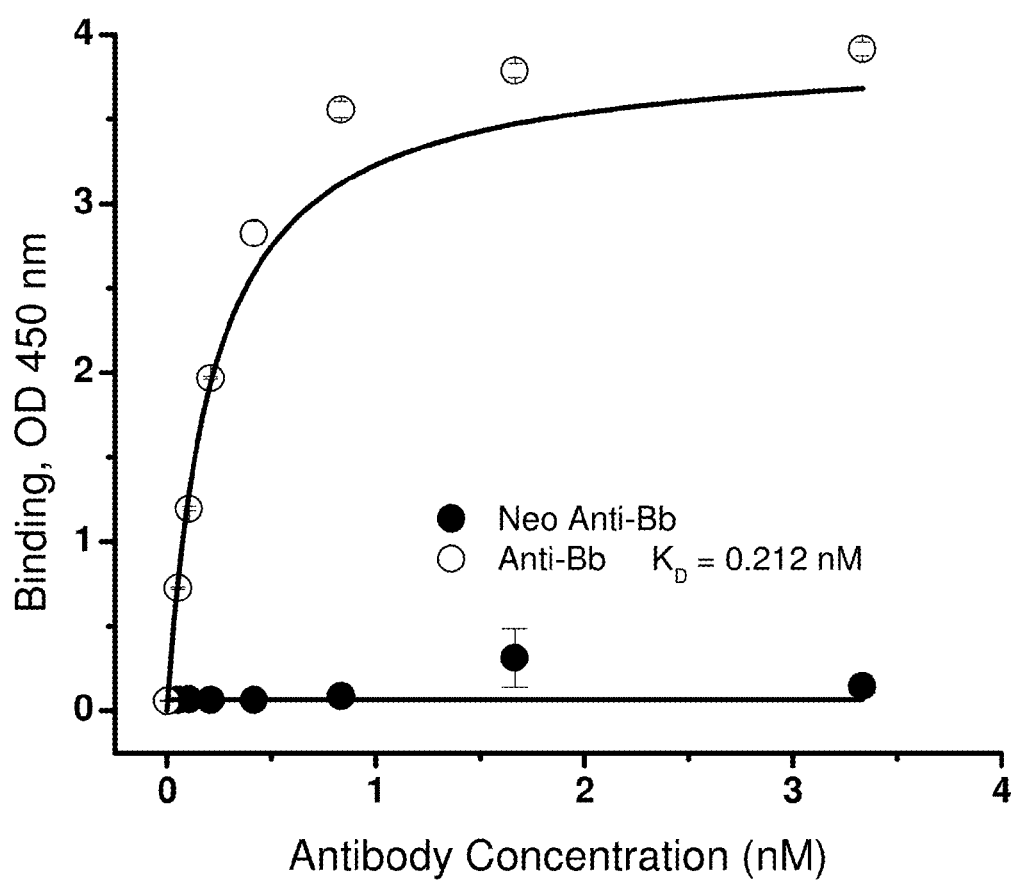
FIG. 3 shows the binding characteristics of Anti-Bb and Neo Anti-Bb in relation to Factor B.

Neo anti-Bb does not bind substrate-coated factor B suggesting that the neoepitope is not expressed on factor B. The apparent binding constant from these data, defined as the concentration of non-neo anti-Bb to reach half-maximal binding, is approximately 212 pM. The data is shown in FIG. 3. Neo anti-Bb appears to be specific to a neoepitope only on Bb.

Example 4: Neo Anti-SC5b-9 Binds Only Polymeric C9 and SC5b-9

Neo anti-C5b-9 recognizes substrate-bound C9 with 1.12 nM affinity. Substrate-bound C9 functions similarly to polymeric C9 in the SC5b-9 complex. Polymeric C9 contains a neoepitope that is formed upon complement pathway activation. The neoantibody binds an epitope formed by polymeric C9 in the SC5b-9 complex. Neo anti-SC5b-9 antibody binds substrate-bound (polymeric) C9 with an affinity of 1.12 nM as compared to the binding affinity of this antibody to SC5b-9 which is 585 pM. This neoantibody did not bind substrate-bound C5, C6, C7, and C8 proteins.

Polystyrene microtiter plates were coated with human C9 or SC5b-9 (Complement Technology) at (0.5 μg/50 μl/well) in PBS overnight at 4° C. After aspirating the protein solutions, wells were blocked with PBS containing 1.0% BSA (Sigma-Aldrich) for 1 hour at room temperature. Wells without protein coating were similarly blocked and served as background controls. Aliquots of neo anti-SC5b-9 (Quidel Corporation) at varying concentrations in blocking solution were added to the wells. Following a 1 hour incubation at room temperature, the wells were washed with PBS.

Protein-bound neo anti-SC5b-9 was detected by the addition of peroxidase-conjugated goat anti-mouse antibody at 1:2000 dilution. Following a 1 hour incubation at room temperature, the plate was washed and 100 μl of TMB substrate (Kirkegaard & Perry Laboratories) was added. After incubation for 30 minutes at room temperature, the TMB reaction was quenched by the addition of 100 μl of 1 M phosphoric acid, and the plate was read at 450 nm on a microplate reader (SPECTRAMAX 250, Molecular Devices). Neo anti-SC5b-9 bound both C9 and SC5b-9 with high affinity, which was calculated using Microcal Origin.

Figure 4:
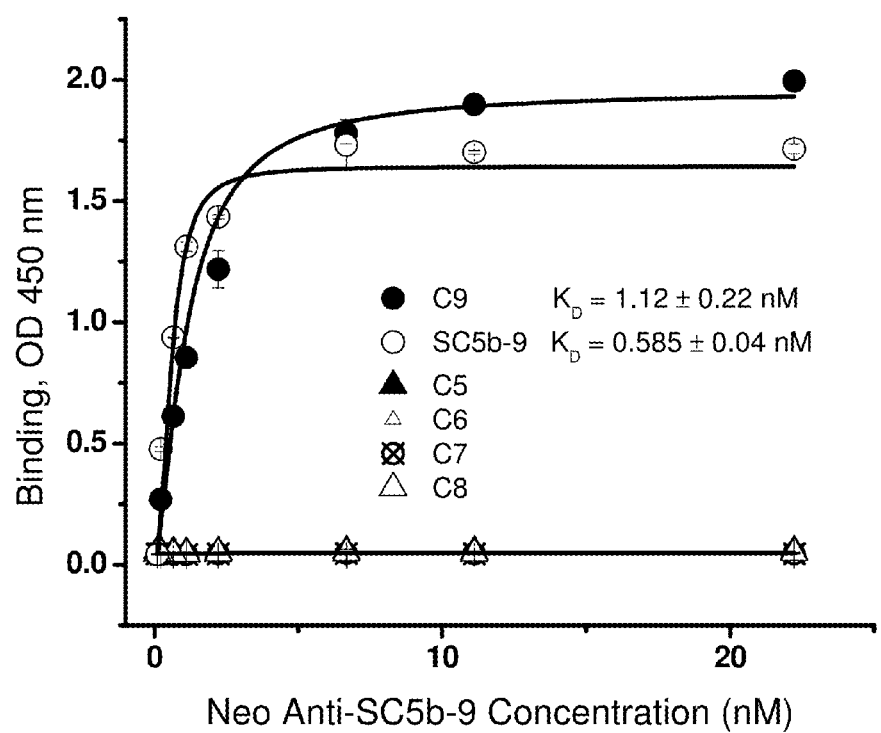
FIG. 4 shows the binding characteristics of Neo Anti-SC5b-9, wherein Neo Anti-SC5b-9 binds only to Polymeric C9 and SC5b-9.

Neo anti-SC5b-9 binds to SC5b-9 with an affinity of 585 pM and polymeric C9 with an affinity of 1120 pM. The apparent binding constant from these data, defined as the concentration of neo anti-SC5b-9 to reach half-maximal binding, is high affinity. The data is shown in FIG. 4.

Example 5: Binding of Anti-C5, -C6, -C7, -C8, and -C9 to Respective Proteins

Figure 5:
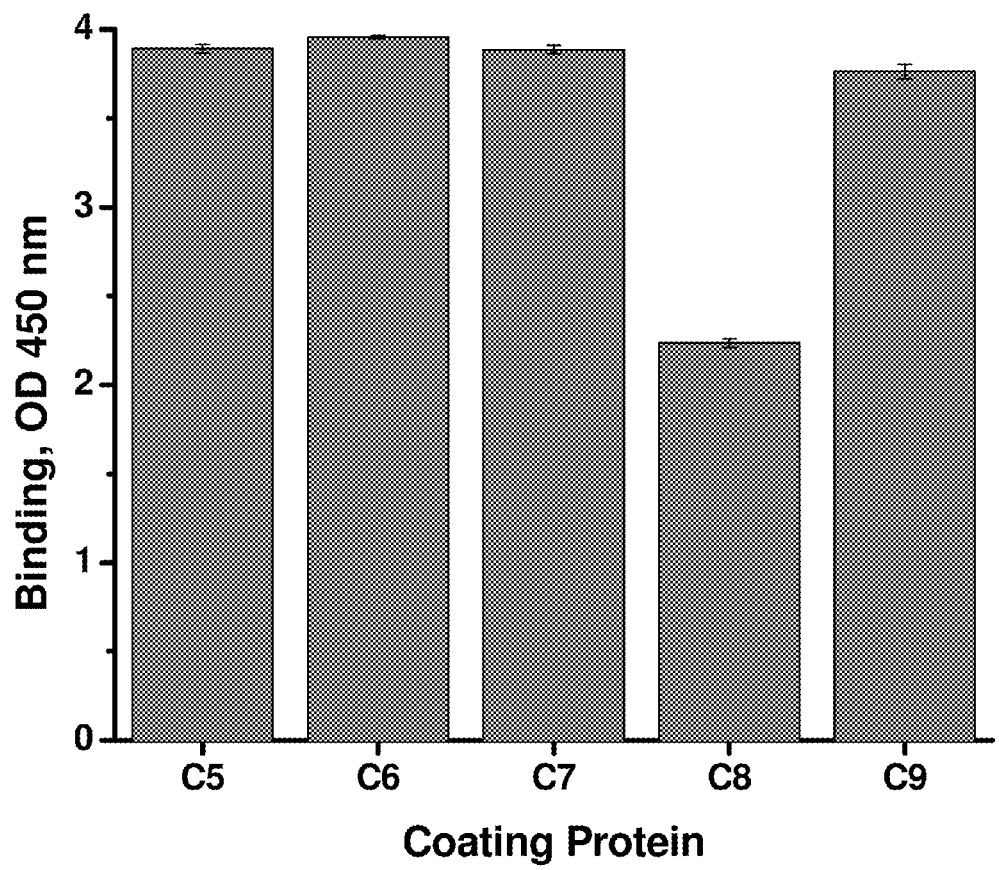
FIG. 5 shows the relationship between the binding characteristics of C5, C6, C7, C8, and C9 to Anti-C5, Anti-C6, Anti-C7, Anti-C8, and Anti-C9.

To ensure that C5, C6, C7, C8, and C9 proteins were bound to the ELISA plate in Example 4, we detected these proteins with their respective antibodies. Anti-C5, -C6, -C7, -C8, and -C9 were allowed to bind the substrate-bound proteins. As shown in FIG. 5, the antibodies bound respective antigens with similar affinities. A single concentration plot is shown in FIG. 5.

Polystyrene microtiter plates were coated with C5, C6, C7, C8, and C9 (Complement Technology) at (1.0 µg/50 µl/well) in PBS overnight at 4° C. After aspirating the protein solutions, wells were blocked with PBS containing 1.0 BSA (Sigma-Aldrich) for 1 hour at room temperature. Wells without protein coating were similarly blocked and served as background controls. Aliquots of respective antibodies (Quidel Corporation) at varying concentrations in blocking solution were added to the wells. Following a 1 hour incubation at room temperature, the wells were washed with PBS.

Antigen-bound antibodies were detected by the addition of peroxidase-conjugated goat anti-mouse antibody at 1:2000 dilution. Following a 1 hour incubation at room temperature, the plate was washed and 100 µl of TMB substrate (Kirkegaard & Perry Laboratories) was added. After incubation for 30 minutes at room temperature, the TMB reaction was quenched by the addition of 100 µl of 1 M phosphoric acid, and the plate was read at 450 nm on a microplate reader (SPECTRAMAX 250, Molecular Devices). Saturation binding curves were generated and a single concentration near saturation was plotted for all antibodies to show comparison. The data are shown in FIG. 5.

As shown in FIG. 5, all antibodies, anti-C5, anti-C6, anti-C7, anti-C8 and anti-C9 are fully active and demonstrate good binding to respective antigens.

Example 6: Binding of Anti-C5, to Substrate-Bound C5 and SCSb-9

Figure 6:
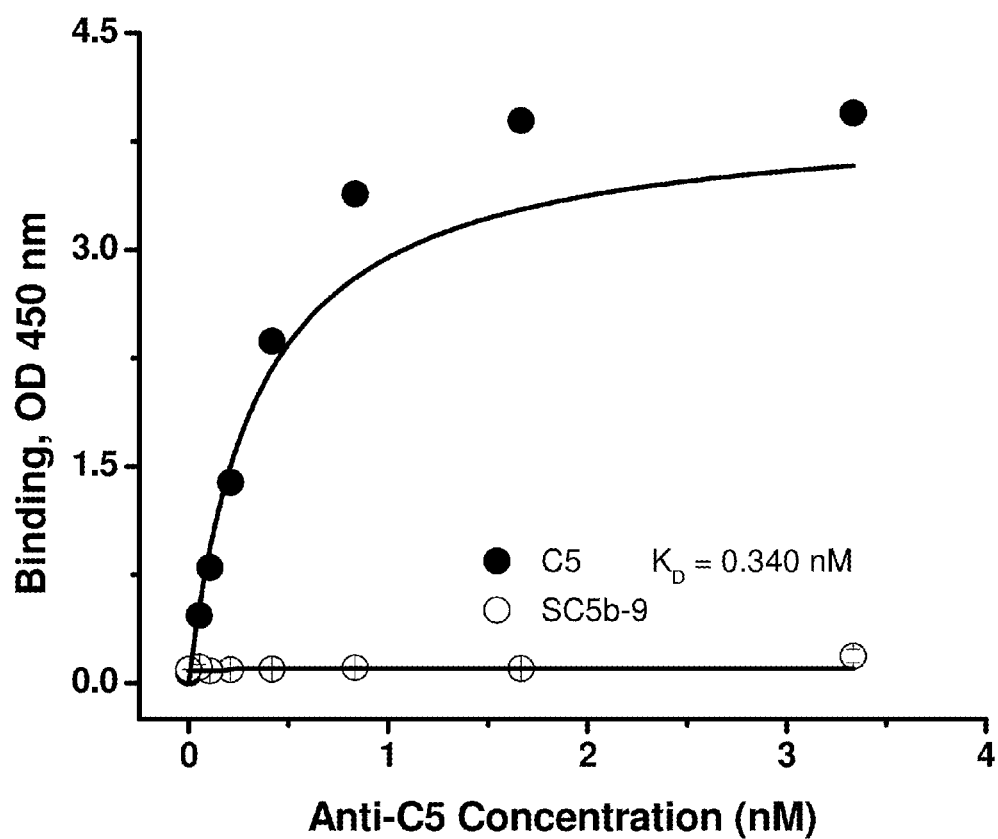
FIG. 6 shows the binding characteristics of Anti-C5, wherein in Anti-C5 binds with C5 but not SC5b-9.

As shown in FIG. 6, anti-C5 binds C5 but does not detect C5b in the SCSb-9 complex suggesting that anti-C5 cannot detect tissue damage caused by C5b-9. This invention selects the neoantibodies that recognize neoepitopes on SCSb-9 or C5b-9.

Polystyrene microtiter plates were coated with C5 and SCSb-9 (Complement Technology) at (0.5 µg/50 µl/well) in PBS overnight at 4° C. After aspirating the protein solutions, wells were blocked with PBS containing 1.0% BSA (Sigma-Aldrich) for 1 hour at room temperature. Wells without protein coating were similarly blocked and served as background controls. Aliquots of anti-C5 (Quidel Corporation) at varying concentrations in blocking solution were added to the wells. Following a 1 hour incubation at room temperature, the wells were washed with PBS.

C5 and SC5b-9 bound antibodies were detected by the addition of peroxidase-conjugated goat anti-mouse antibody at 1:2000 dilution. Following a 1 hour incubation at room temperature, the plate was washed and 100 µl of TMB substrate (Kirkegaard & Perry Laboratories) was added. After incubation for 30 minutes at room temperature, the TMB reaction was quenched by the addition of 100 µl of 1 M phosphoric acid, and the plate was read at 450 nm on a microplate reader (SPECTRAMAX 250, Molecular Devices). Saturation binding curves were generated and a single concentration near saturation was plotted for all antibodies to show comparison.

As shown in FIG. 6, anti-C5 recognizes substrate-bound C5 but not SC5b-9. Therefore, anti-C5 cannot detect complement-mediated tissue damage.

Example 7: Binding of Anti-C6 to Substrate-Bound C6 and SC5b-9

Figure 7:
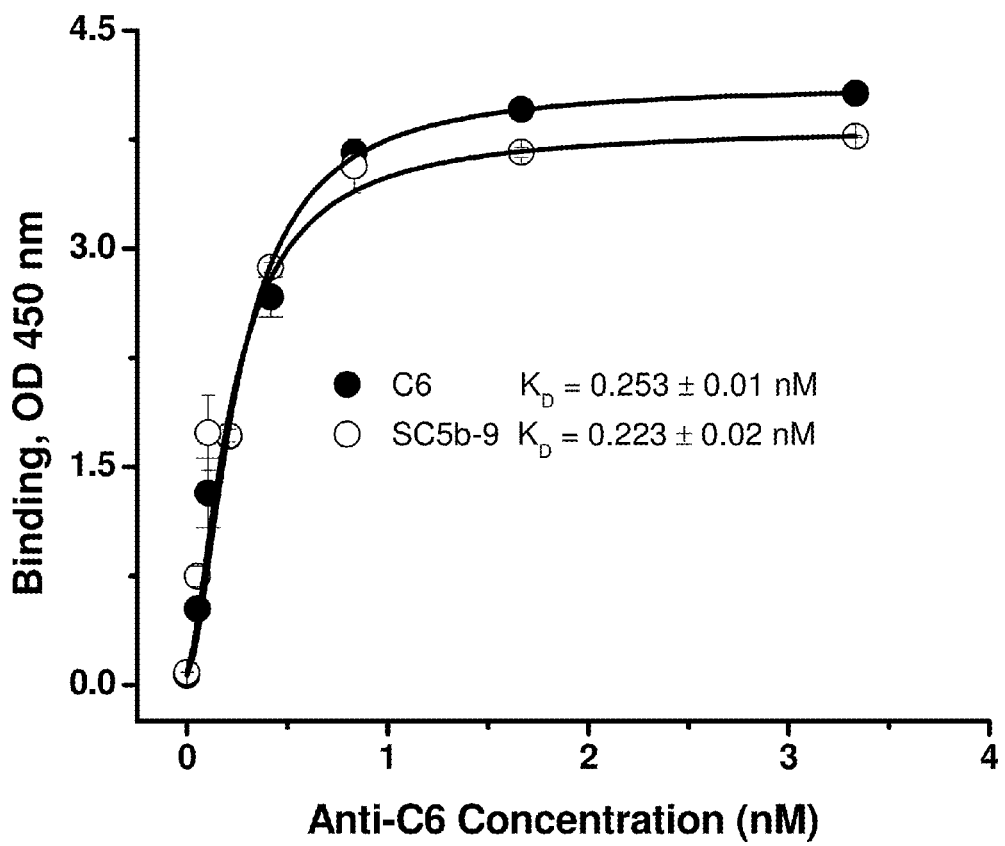
FIG. 7 shows the binding characteristics of Anti-C6, wherein in Anti-C6 binds with C6 and SC5b-9.

As shown in FIG. 7, anti-C6 binds C6 and SC5b-9 complex with similar affinity of approximately 200 pM suggesting that anti-C6 will detect both C6 and SC5b-9 and will not distinguish between C5b-9 and free C6.

Polystyrene microtiter plates were coated with C6 and SC5b-9 (Complement Technology) at (0.5 µg/50 µl well) in PBS overnight at 4° C. After aspirating the protein solutions, wells were blocked with PBS containing 1.0 BSA (SigmaAldrich) for 1 hour at room temperature. Wells without protein coating were similarly blocked and served as background controls. Aliquots of anti-C6 (Quidel Corporation) at varying concentrations in blocking solution were added to the wells. Following a 1 hour incubation at room temperature, the wells were washed with PBS.

C6 and SC5b-9 bound antibodies were detected by the addition of peroxidase-conjugated goat anti-mouse antibody at 1:2000 dilution. Following a 1 hour incubation at room temperature, the plate was washed and 100 µl of TMB substrate (Kirkegaard & Perry Laboratories) was added. After incubation for 30 minutes at room temperature, the TMB reaction was quenched by the addition of 100 µl of 1 M phosphoric acid, and the plate was read at 450 nm on a microplate reader (SPECTRAMAX 250, Molecular Devices). Saturation binding curves were generated and a single concentration near saturation was plotted for all antibodies to show comparison.

As shown in FIG. 7, anti-C6 recognizes both substrate-bound C6 and SC5b-9. Therefore, anti-C6 cannot detect tissue damage specifically.

Example 8: Binding of Anti-C7 to Substrate-Bound C7 and SC5b-9

Figure 8:
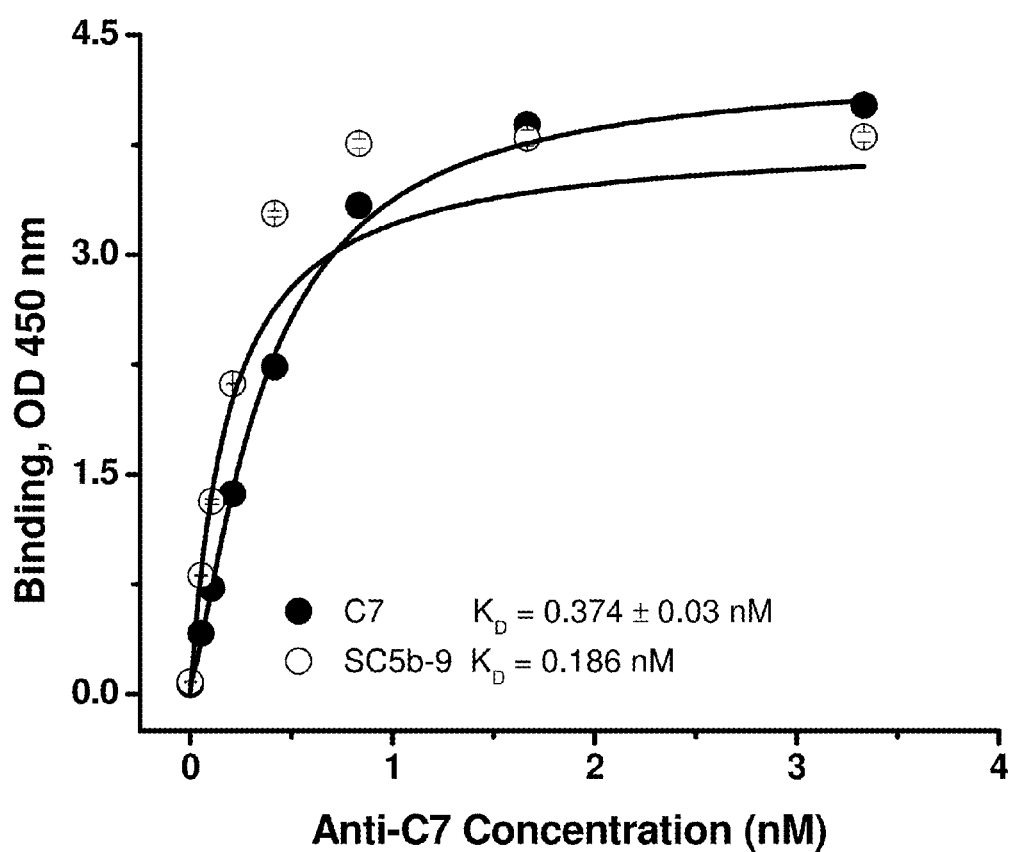
FIG. 8 shows the binding characteristics of Anti-C7, wherein in Anti-C7 binds with C7 and SC5b-9.

As shown in FIG. 8, anti-C7 binds C7 and SC5b-9 complex with ranging from 200-400 pM suggesting that anti-C7 will detect both C7 and SC5b-9 and will not distinguish between SC5b-9 and free C7.

Polystyrene microtiter plates were coated with C7 and SC5b-9 (Complement Technology) at (0.5 µg/50 µl well) in PBS overnight at 4° C. After aspirating the protein solutions, wells were blocked with PBS containing 1.0% BSA (Sigma-Aldrich) for 1 hour at room temperature. Wells without protein coating were similarly blocked and served as background controls. Aliquots of anti-C7 (Quidel Corporation) at varying concentrations in blocking solution were added to the wells. Following a 1 hour incubation at room temperature, the wells were washed with PBS.

C7 and SC5b-9 bound antibodies were detected by the addition of peroxidase-conjugated goat anti-mouse antibody at 1:2000 dilution. Following a 1 hour incubation at room temperature, the plate was washed and 100 µl of TMB substrate (Kirkegaard & Perry Laboratories) was added. After incubation for 30 minutes at room temperature, the TMB reaction was quenched by the addition of 100 µl of 1 M phosphoric acid, and the plate was read at 450 nm on a microplate reader (SPECTRAMAX 250, Molecular Devices). Saturation binding curves were generated and a single concentration near saturation was plotted for all antibodies to show comparison.

As shown in FIG. 8, anti-C7 recognizes both substrate-bound C7 and SC5b-9. Therefore, anti-C7 cannot detect tissue damage specifically.

Example 9: Binding of Anti-C8 to Substrate-Bound C8 and SC5b-9

Figure 9:
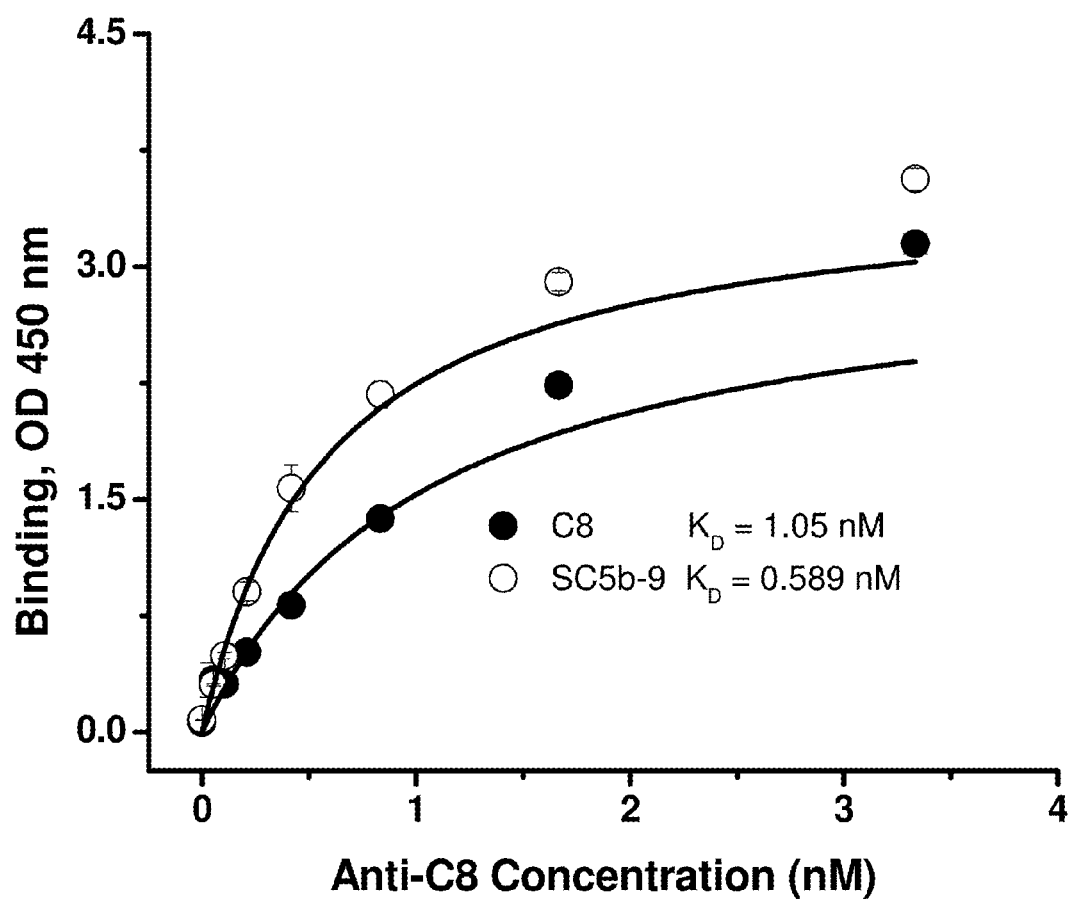
FIG. 9 shows the binding characteristics of Anti-C8, wherein in Anti-C8 binds with C8 and SC5b-9.

As shown in FIG. 9, anti-C8 binds C8 and SC5b-9 complex with affinity ranging from 600-1000 pM suggesting that anti-C8 will detect both C8 and SC5b-9 and will not distinguish between SC5b-9 and free C8.

Polystyrene microtiter plates were coated with C8 and SC5b-9 (Complement Technology) at (0.5 µg/50 µl/well) in PBS overnight at 4° C. After aspirating the protein solutions, wells were blocked with PBS containing 1.0 BSA (Sigma-Aldrich) for 1 hour at room temperature. Wells without protein coating were similarly blocked and served as background controls. Aliquots of anti-C8 (Quidel Corporation) at varying concentrations in blocking solution were added to the wells. Following a 1 hour incubation at room temperature, the wells were washed with PBS.

C8 and SC5b-9 bound antibodies were detected by the addition of peroxidase-conjugated goat anti-mouse antibody at 1:2000 dilution. Following a 1 hour incubation at room temperature, the plate was washed and 100 µl of TMB substrate (Kirkegaard & Perry Laboratories) was added. After incubation for 30 minutes at room temperature, the TMB reaction was quenched by the addition of 100 µl of 1 M phosphoric acid, and the plate was read at 450 nm on a microplate reader (SPECTRAMAX 250, Molecular Devices). Saturation binding curves were generated and a single concentration near saturation was plotted for all antibodies to show comparison.

As shown in FIG. 9, anti C8, recognizes both substrate-bound C8 and SC5b-9. Therefore, anti-C8 cannot detect tissue damage specifically.

Example 10: Binding of Anti-C9 to Substrate-Bound C9 and SC5b-9

Figure 10:
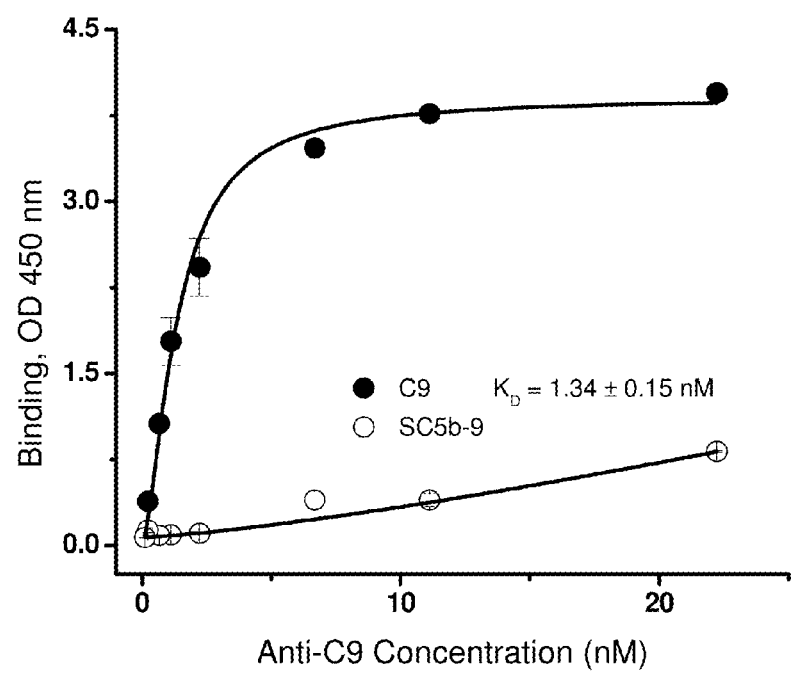
FIG. 10 shows the binding characteristics of Anti-C9, wherein in Anti-C9 binds with C9 but not SC5b-9.

As shown in FIG. 10, anti-C9 binds C9 but not the SC5b-9 complex suggesting that anti-C9 will not detect tissue damage as it does not recognize SC5b-9.

Polystyrene microtiter plates were coated with C9 and SC5b-9 (Complement Technology) at (1 µg/50 µl/well) in PBS overnight at 4° C. After aspirating the protein solutions, wells were blocked with PBS containing 1.0% BSA (Sigma-Aldrich) for 1 hour at room temperature. Wells without protein coating were similarly blocked and served as background controls. Aliquots of anti-C9 (Quidel Corporation) at varying concentrations in blocking solution were added to the wells. Following a 1 hour incubation at room temperature, the wells were washed with PBS.

C9 and SC5b-9 bound antibodies were detected by the addition of peroxidase-conjugated goat anti-mouse antibody at 1:2000 dilution. Following a 1 hour incubation at room temperature, the plate was washed and 100 µl of TMB substrate (Kirkegaard & Perry Laboratories) was added. After incubation for 30 minutes at room temperature, the TMB reaction was quenched by the addition of 100 µl of 1 M phosphoric acid, and the plate was read at 450 nm on a microplate reader (SPECTRAMAX 250, Molecular Devices). Saturation binding curves were generated and a single concentration near saturation was plotted for all antibodies to show comparison.

As shown in FIG. 10, antiC9 recognizes substrate-bound C9 but not SC5b-9. Therefore, anti-C9 cannot detect tissue damage caused by SC5b-9.

Example 11: Neo Anti-Polymeric C9 Binds Polymeric C9 and SC5b-9

Neo anti-polymeric C9 recognizes substrate-bound C9 with 1.12 nM affinity. Substrate-bound C9 can exhibit the characteristics of polymeric C9 as well. Because it is an artificially created polymeric C9, the C9 may be present as a monomer or polymer. The substrate-bound C9 can resemble polymerized C9. Polymeric C9 contains a neoepitope that is formed upon activation. The neo anti-polymeric C9 antibody binds polymeric C9 and polymeric C9 in the SC5b-9 complex. The neo anti-polymeric C9 antibody binds substrate-bound (polymeric) C9 with an affinity of 1.12 nM as compared to the binding affinity of this antibody to SC5b-9 which is 585 pM. This antibody was not observed to bind substrate-bound C5, C6, C7, and C8 proteins.

Polystyrene microtiter plates were coated with human C9 or SC5b-9 (Complement Technology) at (0.5 µg/50 µl/well) in PBS overnight at 4° C. After aspirating the protein solutions, wells were blocked with PBS containing 1.0% BSA (Sigma-Aldrich) for 1 hour at room temperature. Wells without protein coating were similarly blocked and served as background controls. Aliquots of neo anti-SC5b-9 (Quidel Corporation) at varying concentrations in blocking solution were added to the wells. Following a 1 hour incubation at room temperature, the wells were washed with PBS.

Substrate-coated C5b-9 and C9 bound neo anti C5b-9 was detected by the addition of peroxidase-conjugated goat anti-mouse antibody at 1:2000 dilution. Following a 1 hour incubation at room temperature, the plate was rinsed and 100 µl of TMB substrate (Kirkegaard & Perry Laboratories) was added. After incubation for 30 minutes at room temperature, the TMB reaction was quenched by the addition of 100 µl of 1 M phosphoric acid, and the plate was read at 450 nm on a microplate reader (SPECTRAMAX 250, Molecular Devices). Neo anti-SC5b-9 binds both C9 and SC5b-9 with high affinity, calculated using Microcal Origin.

Figure 11:
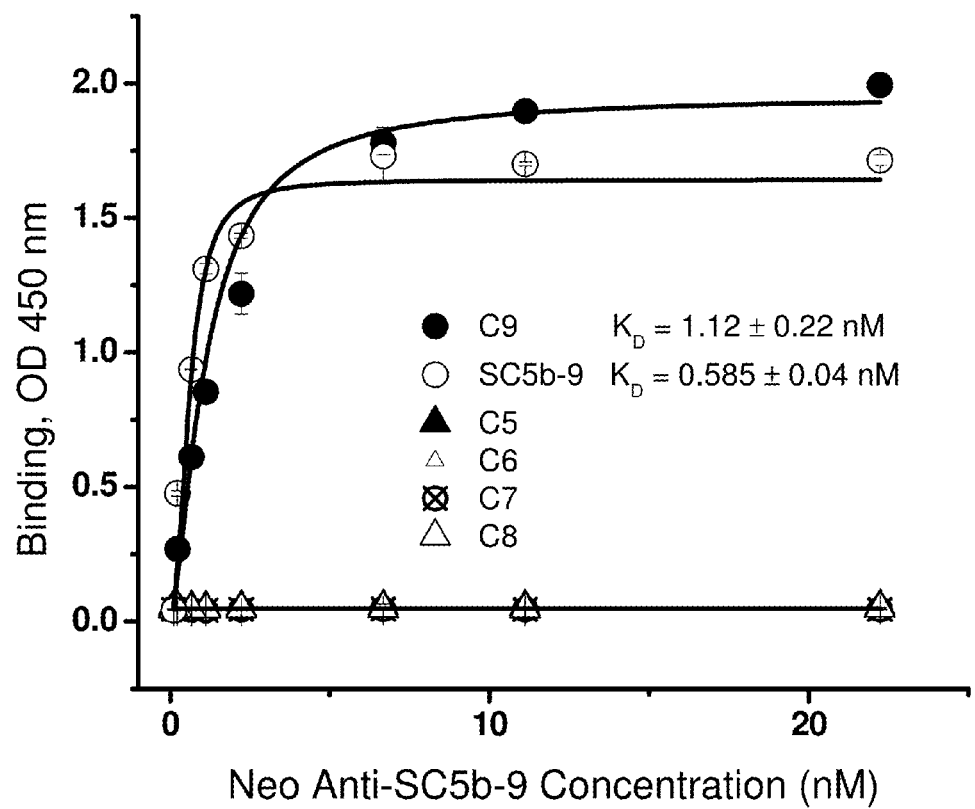
FIG. 11 shows the binding characteristics of Neo Anti-Polymeric C9, wherein Neo Anti-Polymeric C9 binds with Polymeric C9 and SC5b-9.

Neo anti-polymeric C9 binds to SC5b-9 with an affinity of 585 pM and polymeric C9 with an affinity of 1120 pM. The apparent binding constant from these data, defined as the concentration of neo anti-polymeric C9 to reach half-maximal binding, is high affinity. The data is shown in FIG. 11.

Example 12: Anti-Polymeric C9 Antibody Detects Substrate-Bound SC5b-9 in the Presence of Normal Human Serum The results from FIGS. 1 through 11 demonstrate that neoantibodies specifically detect tissue damage as represented by the formation of polymeric C9. For example, neo anti-iC3b, neo anti-C3d, neo anti-Bb, and neo anti-polymeric C9 detect AP activation at various steps in the complement pathway. Neo anti-polymeric C9 detect the final step of AP activation. The presence of polymeric C9 is indicative of tissue damage because the C5b-9 complex is responsible for cell lysis. To ensure that neo anti-polymeric C9 specifically bind polymeric C9 in vivo, a competition assay was performed. This assay used an excess of normal human serum to compete with substrate-bound SC5b-9 for binding to neo anti-polymeric C9. Normal human serum did not inhibit the binding of neo anti-polymeric C9 to substrate-bound SC5b-9 at as high as 50% of physiological serum concentrations. Therefore, neo anti-polymeric C9 is specific to C5b-9 in vivo, and does not bind the free complement proteins present in serum. The amount of C9 normally present in serum is 60 µg/ml. The highest concentration of serum used in this study was 50% which translates to 30 µg/ml of C9. In terms of nM, the concentrations of C9 in the serum used for each dilution are: 422 nM, 253 nM, 126 nM, 42 nM, 25 nM, 12 nM, 4.2 nM, 2.5 nM, 1.3 nM, 0.42 nM, and 0 nM.

Neo anti-polymeric C9 but not anti-monomeric C9 detects the neoantigen SC5b-9. This suggests that the polymeric C9 antibody specifically detects substrate-bound SC5b-9. This polymeric C9 antibody does not recognize the free or monomeric C9 and therefore is target specific to a neoepitope expressed by C5b-9. Anti-monomeric C9 antibody binds only free C9 but does not recognize SC5b-9.

In this model, an ELISA well is coated with SC5b-9 to represent tissue containing the C5b-9 complex. This coated plate is then incubated with various concentrations of normal human serum containing and a fixed concentration of neo anti-polymeric C9. The neoantibody will bind SC5b-9 and therefore will be specific for C5b-9 in vivo.

In this experiment, polystyrene microtiter plates were coated with SC5b-9 or C9 at 0.5 µg/50 µl/well) (Complement Technology) in PBS overnight at 4° C. After aspirating the protein solution, wells were blocked with PBS containing 1.0% BSA (Sigma-Aldrich) for 1 hour at room temperature. Wells without protein coating were similarly blocked and served as background controls. A fixed concentration of neo anti-SC5b-9 (Quidel Corporation) was mixed with varying concentrations of normal human serum in blocking solution. Following a 1 hour incubation at room temperature, the wells were washed with PBS. Neo anti-polymeric C9 that bound SC5b-9 was detected by the addition of peroxidase-conjugated goat anti-mouse antibody at 1:2000 dilution. Following a 1 hour incubation at room temperature, the plate was washed and 100 µl of TMB substrate (Kirkegaard & Perry Laboratories) was added. After incubation for 30 minutes at room temperature, the TMB reaction was quenched by the addition of 100 µl of 1 M phosphoric acid, and the plate was read at 450 nm on a micro plate reader (SPECTRAMAX 250, Molecular Devices). Free C9 present in serum or elsewhere would not affect the specific binding of neo anti-polymeric C9 binding to the C5b-9 complex.

Figure 12:
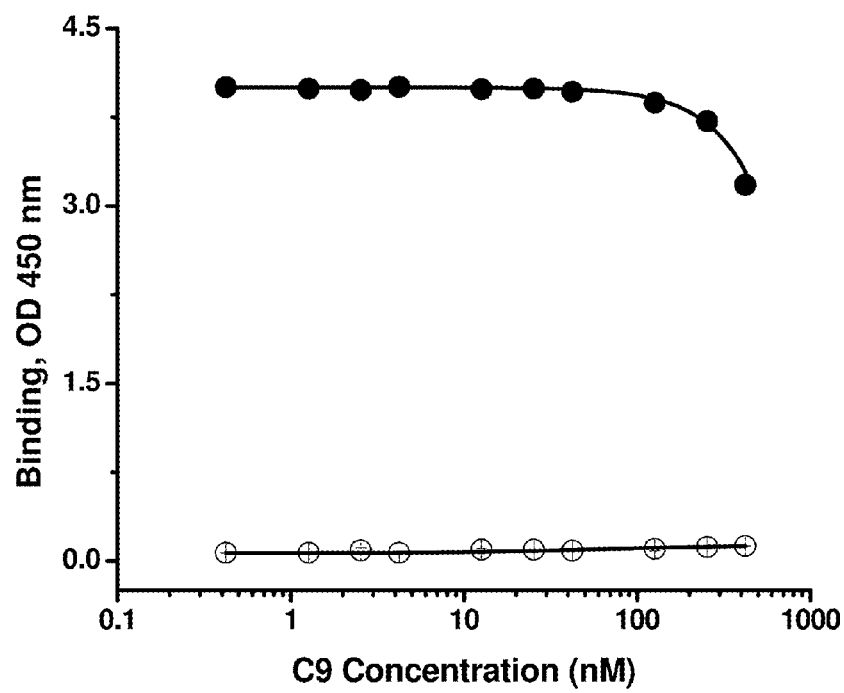
FIG. 12 shows the binding characteristics of Anti-Polymeric C9, wherein Anti-Polymeric C9 detection of Substrate-Bound SC5b-9 is not inhibited by proteins in Human Serum.

As shown in FIG. 12, the binding of neo anti-polymeric C9 to SC5b-9 was not inhibited by normal human serum. This suggests that neo anti-polymeric C9 can be used to detect tissue damage in vivo.

Example 13: Neo Anti-Polymeric C9 Detects Deposited C5b-9 from Normal Human Serum To determine if neo anti-polymeric binds deposited C5b-9 formed from normal human serum, an in vitro assay was used. In this assay, wells coated with lipopolysaccharide (LPS) were incubated with 50%, 30%, 20%, 10%, 8%, 6%, 4%, and 0% normal human serum in buffer that allowed alternative pathway (AP) activation. LPS is known to activate the alternative pathway, and as a result C5b-9 is formed on the surface of LPS. Anti-C5, anti-C6, anti-C7, anti-C8, anti-C9, and neo anti-polymeric C9 were used to detect the newly deposited C5b-9. Anti-C6, anti-C7, anti-C8 were able to detect deposited C5b-9. Further, neo anti-polymeric C9 but not anti-monomeric C9 detected deposited C5b-9. Neo anti-polymeric C9 bound C5b-9 with a high affinity illustrating that this antibody would be an effective way to detect C5b-9 formed in vivo.

Figure 13:
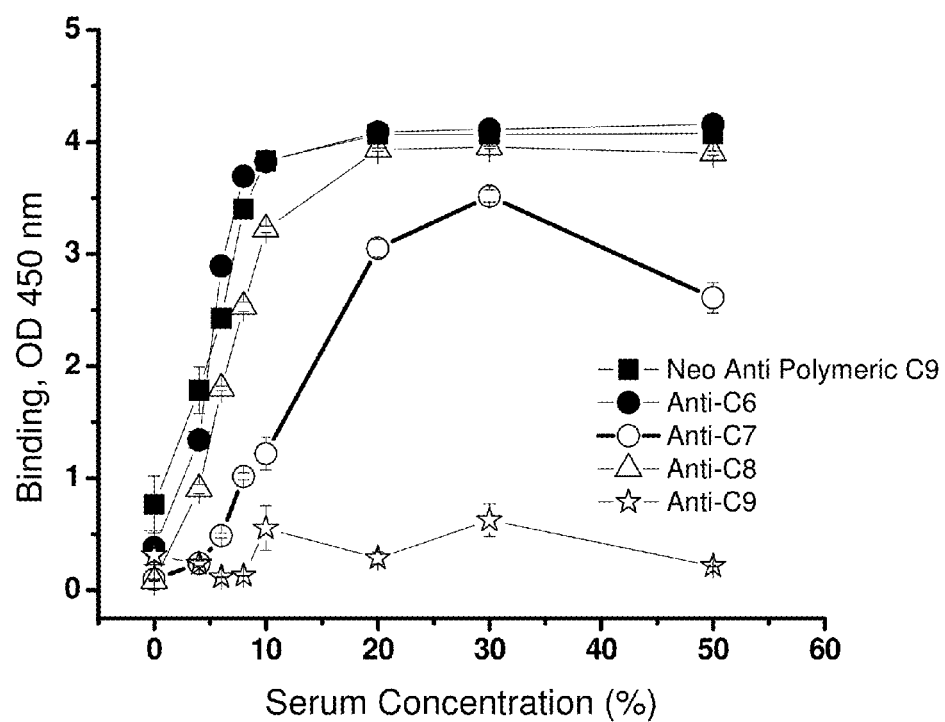
FIG. 13 shows the binding characteristics of Neo Anti-Polymeric C9, Anti-C6, Anti-C7, and Anti-C8, wherein these antibodies detected the MAC complex.

As shown in FIG. 13, Neo anti-polymeric C9 detected C5b-9 specifically even in the presence of normal human serum.

Example 14: Neo Anti-Polymeric C9 Antibody Detects Deposited C5b-9 in Pathological Drusen Eyes were procured from an AMD patient through an eye bank under an approved IRB. Paraffin blocks were prepared and sections cut that displayed macula. The sections were stained using neo anti-polymeric C9. As shown in FIG. 14, neo anti-polymeric C9 detected drusen via polymeric C9 deposition in tissue from AMD patients. Therefore, the individual who was categorized as normal may be at risk for AMD.

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

Having described the invention the following is claimed:

1. A method for diagnosing the development of a tissue injury in a subject in vivo, comprising:
   administering to tissue of the subject in vivo a sample of neoantibodies or fragments thereof that bind to neo-epitopes of C5b-9/SC5b-9 deposited on the tissue of the subject; and
   detecting the amount of neoantibodies bound to the neo-epitopes of the neo-epitope bearing complement proteins or fragments deposited on the tissue of the subject in vivo, wherein the amount of neoantibodies bound to the C5b-9/SC5b-9 deposited on the tissue of the subject is indicative of complement activation and is substantially elevated in a subject with tissue injury compared to baseline levels in a control population of subjects without tissue injury.

2. The method of claim 1, wherein the tissue injury is the result of a disease to a tissue.

3. The method of claim 1, wherein the neoantibody is a scFv, Diabody, minibody, ScFv-Fc and intact antibody, Fab or Fab'.

4. The method of claim 1, wherein the neo-epitope bearing complement proteins or fragments are selected from the group consisting of C3b, iC3b, C3dg, C3d, C4d, Ba, Bb, C5b, and C5b-9/SC5b-9.

5. The method of claim 1, wherein neoantibody is a neo anti-C5b-9 antibody or fragment thereof.

6. The method of claim 5, wherein the neo anti-C5b-9 not does not bind to C5, C6, C7, C8, and C9.

7. The method of claim 4, wherein the neo anti-C5b-9 antibody can bind to polymeric C9, but not with the monomeric C9.

8. The method of claim 1, wherein the neoantibody is labeled with a label, contrast agent, or imaging agent that is detected to determine detection of the labeled neoantibody administered to the tissue.

9. The method of claim 4, wherein the label can be selected from the group consisting of a radioactive or non radioactive trace, Tc99, immunoPet, and two photon imaging agents.

10. The method of claim 1, wherein the tissue is in the human body and selected from the group consisting of liver, kidney, heart, gut, pancreas, or the eye.

11. The method of claim 2, wherein the tissue is in the eye.

12. The method of claim 1, wherein the step of detecting the neoantibody includes:
   measuring the amount of bound neoantibody using an imaging technique to obtain a binding value for each neoantibody bound to a neo-epitope; and
   correlating the values determined by measuring the amount of bound neoantibody from which is calculated a value for the amount of a particular neoantibody bound to neo-epitope of the complement protein or fragment present in the tissue.

13. The method of claim 1, further comprising administering to the tissue a labeled secondary antibody that binds to the neoantibody administered to the tissue and forms a detectable complex.

14. The method of claim 1, wherein the neoantibody is an anti-polymeric C9 antibody that binds to polymeric C9 bearing complement complexes in the tissue.

15. The method of claim 1, wherein the neo anti-iC3b antibody does not bind to C3c or C4d.

16. The method of claim 1, wherein the neo anti-C3d antibody does not bind to C3c.

17. A method for diagnosing the development of a tissue injury in a subject in vivo, comprising:
   administering to tissue of the subject in vivo a sample of neoantibodies or fragments thereof that bind to neo-epitopes of neo-epitope bearing complement proteins or fragments deposited on the tissue of the subject, wherein neoantibody comprises a neo anti-C5b-9 antibody or fragment thereof that does not bind to C5, C6, C7, C8, and C9 wherein the neoantibodies or fragments thereof are labeled for in vivo detection; and
   detecting the amount of neoantibodies bound to the neo-epitopes of the neo-epitope bearing complement proteins or fragments deposited on the tissue of the subject in vivo, wherein the amount of neoantibodies bound to the neo-epitope bearing complement proteins or fragments deposited on the tissue of the subject is indicative of complement activation and is substantially elevated in a subject with tissue injury compared to baseline levels in a control population of subjects without tissue injury.

18. The method of claim 17, wherein the neoantibody is an anti-polymeric C9 antibody that binds to polymeric C9 bearing complement complexes in the tissue.

* * * * *